(12) United States Patent
Ninomiya

(10) Patent No.: US 10,996,747 B2
(45) Date of Patent: May 4, 2021

(54) LINE-OF-SIGHT DETECTION DEVICE, LINE-OF-SIGHT DETECTION METHOD, AND MEDIUM

(71) Applicant: JVCKENWOOD Corporation, Yokohama (JP)

(72) Inventor: Masaru Ninomiya, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 71 days.

(21) Appl. No.: 16/561,184

(22) Filed: Sep. 5, 2019

(65) Prior Publication Data
US 2019/0391643 A1 Dec. 26, 2019

Related U.S. Application Data

(63) Continuation of application No. PCT/JP2017/040639, filed on Nov. 10, 2017.

(30) Foreign Application Priority Data

Mar. 24, 2017 (JP) .............................. JP2017-059712

(51) Int. Cl.
*G06F 3/00* (2006.01)
*G06F 3/01* (2006.01)
(Continued)

(52) U.S. Cl.
CPC ........... *G06F 3/013* (2013.01); *G06K 9/0061* (2013.01); *G06K 9/00248* (2013.01); *G06T 7/73* (2017.01); *G06T 2207/30201* (2013.01)

(58) Field of Classification Search
CPC .. G06F 3/013; G06K 9/0061; G06K 9/00248; G06T 7/73; G06T 2207/30201; A61B 5/163
See application file for complete search history.

(56) References Cited

U.S. PATENT DOCUMENTS

2016/0113486 A1* 4/2016 Ninomiya ................ A61B 3/14
351/210
2017/0091520 A1* 3/2017 Ishii .................... G06K 9/00617
(Continued)

FOREIGN PATENT DOCUMENTS

JP 02-134130 5/1990

OTHER PUBLICATIONS

International Search Report and Written Opinion for International Patent Application No. PCT/JP2017/040639 dated Jan. 30, 2018, 10 pages.

*Primary Examiner* — Ping Y Hsieh
(74) *Attorney, Agent, or Firm* — Amin, Turocy & Watson, LLP

(57) ABSTRACT

Validity of a line-of-sight direction detected by a gaze point detection unit is determined by using a positional difference that is a calibration value used for detecting a position of a corneal curvature center. Therefore, it is possible to easily and effectively determine the validity of the line-of-sight direction without additionally using a system or the like for detecting the validity of the line-of-sight direction. Consequently, it is possible to accurately detect line-of-sight directions of various subjects, such as a subject whose left and right eyeballs have different corneal curvature radii or a subject whose line-of-sight directions of left and right eyeballs are largely different due to the influence of strabismus or the like.

5 Claims, 13 Drawing Sheets

(51) Int. Cl.
  *G06K 9/00*   (2006.01)
  *G06T 7/73*   (2017.01)

(56) References Cited

U.S. PATENT DOCUMENTS

2017/0105619 A1\* 4/2017 Ebisawa .............. A61B 3/0025
2018/0039327 A1\* 2/2018 Noda ................. H04N 5/23222

\* cited by examiner

LINE-OF-SIGHT DETECTION DEVICE, LINE-OF-SIGHT DETECTION METHOD, AND MEDIUM

CROSS-REFERENCE TO RELATED APPLICATION(S)

This application is a continuation of PCT international application Ser. No. PCT/JP2017/040639 filed on Nov. 10, 2017 which designates the United States, incorporated herein by reference, and which claims the benefit of priority from Japanese Patent Application No. 2017-059712, filed on Mar. 24, 2017, incorporated herein by reference.

BACKGROUND

1. Technical Field

The present disclosure relates to a line-of-sight detection device, a line-of-sight detection method, and a medium.

2. Description of the Related Art

A line-of-sight detection device that detects a position of gaze of an operator or a subject on an observation screen, such as a monitor screen, has been proposed. As a method of detecting a line-of-sight direction of the subject in a non-contact manner without wearing a device on the face of the subject, a method of irradiating an eyeball of the subject with detection light, calculating a pupil center and a corneal curvature center from an image of the eyeball irradiated with the detection light, and detecting a vector from the corneal curvature center to the pupil center as the line-of-sight direction of the subject has been known. Conventionally, the line-of-sight direction is detected based on the assumption that corneal curvature radii of the left and right eyeballs have the same values and line-of-sight directions of the right and left eyeballs are identical (Japanese Patent No. 2739331B).

However, in the conventional technique, it is difficult to accurately detect a line-of-sight direction of a subject whose left and right eyeballs have different corneal curvature radii or a subject whose line-of-sight directions of left and right eyeballs are largely different due to the influence of strabismus or the like, which is a problem.

SUMMARY

It is an object of the present disclosure to at least partially solve the problems in the conventional technology.

A line-of-sight detection device according to the present disclosure includes a display control unit configured to display an image at a single point on a display screen of a display device, a light source configured to irradiate right and left eyeballs of a subject with detection light, an image data acquisition unit configured to acquire image data of the right and left eyeballs of the subject irradiated with the detection light, a position detection unit configured to detect, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs, a curvature center calculation unit configured to calculate a position of a corneal curvature center of each of the right and left eyeballs on the basis of a virtual line connecting the light source and the corneal reflection center and a virtual line connecting the image and the pupil center, a corrected position calculation unit configured to correct the position of the corneal curvature center on the basis of a distance between the pupil center and the corneal curvature center, and calculate a position of the corrected corneal curvature center of each of the right and left eyeballs, an ideal position calculation unit configured to calculate a position of an ideal corneal curvature center of each of the right and left eyeballs from a position of the image displayed at the single point on the display screen and the position of the pupil center, an arithmetic unit configured to calculate a positional difference that is a difference between the position of the corrected corneal curvature center and the position of the ideal corneal curvature center for each of the right and left eyeballs, a gaze point detection unit configured to detect a line-of-sight direction of each of the right and left eyeballs from the position of the pupil center and a position that is obtained by adding the positional difference to the position of the corrected corneal curvature center, and a determination unit configured to determine whether the line-of-sight direction of each of the right and left eyeballs detected by the gaze point detection unit is valid on the basis of a magnitude of a right-left difference that is a difference between the positional differences of the right and left eyeballs.

A line-of-sight detection method according to the present disclosure includes a display control step of displaying an image at a single point on a display screen of a display device, an irradiation step of irradiating right and left eyeballs of a subject with detection light from a light source, an image data acquisition step of acquiring image data of the right and left eyeballs of the subject irradiated with the detection light, a position detection step of detecting, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs, a curvature center calculation step of calculating a position of a corneal curvature center of each of the right and left eyeballs on the basis of a virtual line connecting the light source and the corneal reflection center and a virtual line connecting the image and the pupil center, a corrected position calculation step of correcting the position of the corneal curvature center on the basis of a distance between the pupil center and the corneal curvature center, and calculating a position of the corrected corneal curvature center of each of the right and left eyeballs, an ideal position calculation step of calculating a position of an ideal corneal curvature center of each of the right and left eyeballs from a position of the image displayed at the single point on the display screen and the position of the pupil center, an arithmetic step of calculating a positional difference that is a difference between the position of the corrected corneal curvature center and the position of the ideal corneal curvature center for each of the right and left eyeballs, a gaze point detection step of detecting a line-of-sight direction of each of the right and left eyeballs from the position of the pupil center and a position that is obtained by adding the positional difference to the position of the corrected corneal curvature center, and a determination step of determining whether the line-of-sight direction of each of the right and left eyeballs is valid on the basis of a magnitude of a right-left difference that is a difference between the positional differences of the right and left eyeballs.

A non-transitory storage medium storing a line-of-sight detection program according to the present disclosure therein causes a computer to execute a display control step of displaying an image at a single point on a display screen of a display device, an irradiation step of irradiating right and left eyeballs of a subject with detection light from a light source, an image data acquisition step of acquiring image data of the right and left eyeballs of the subject irradiated with the detection light, a position detection step of detecting, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs, a curvature center calculation step of calculating a position of a corneal curvature center of each of the right and left eyeballs on the basis of a virtual line connecting the light source and the corneal reflection center and a virtual line connecting the image and the pupil center, a corrected position calculation step of correcting the position of the corneal curvature center on the basis of a distance between the pupil center and the corneal curvature center, and calculating a position of the corrected corneal curvature center of each of the right and left eyeballs, an ideal position calculation step of calculating a position of an ideal corneal curvature center of each of the right and left eyeballs from a position of the image displayed at the single point on the display screen and the position of the pupil center, an arithmetic step of calculating a positional difference that is a difference between the position of the corrected corneal curvature center and the position of the ideal corneal curvature center for each of the right and left eyeballs, a gaze point detection step of detecting a line-of-sight direction of each of the right and left eyeballs from the position of the pupil center and a position that is obtained by adding the positional difference to the position of the corrected corneal curvature center, and a determination step of determining whether the line-of-sight direction of each of the right and left eyeballs is valid on the basis of a magnitude of a right-left difference that is a difference between the positional differences of the right and left eyeballs.

The above and other objects, features, advantages and technical and industrial significance of this disclosure will be better understood by reading the following detailed description of presently preferred embodiments of the disclosure, when considered in connection with the accompanying drawings.

DETAILED DESCRIPTION OF THE PREFERRED EMBODIMENTS

Hereinafter, embodiments of the present disclosure will be described with reference to the accompanying drawings, but the present disclosure is not limited thereto. Constituent elements of the embodiments described below may be appropriately combined. In addition, some constituent elements are not used in some cases.

In the following descriptions, positional relationships between parts will be described by setting a three-dimensional global coordinate system. A direction parallel to a first axis of a predetermined plane is defined as an X-axis direction, a direction parallel to a second axis of the predetermined plane perpendicular to the first axis is defined as a Y-axis direction, and a direction parallel to a third axis perpendicular to each of the first axis and the second axis is defined as a Z-axis direction. The predetermined plane includes an XY plane.

Figure 1:
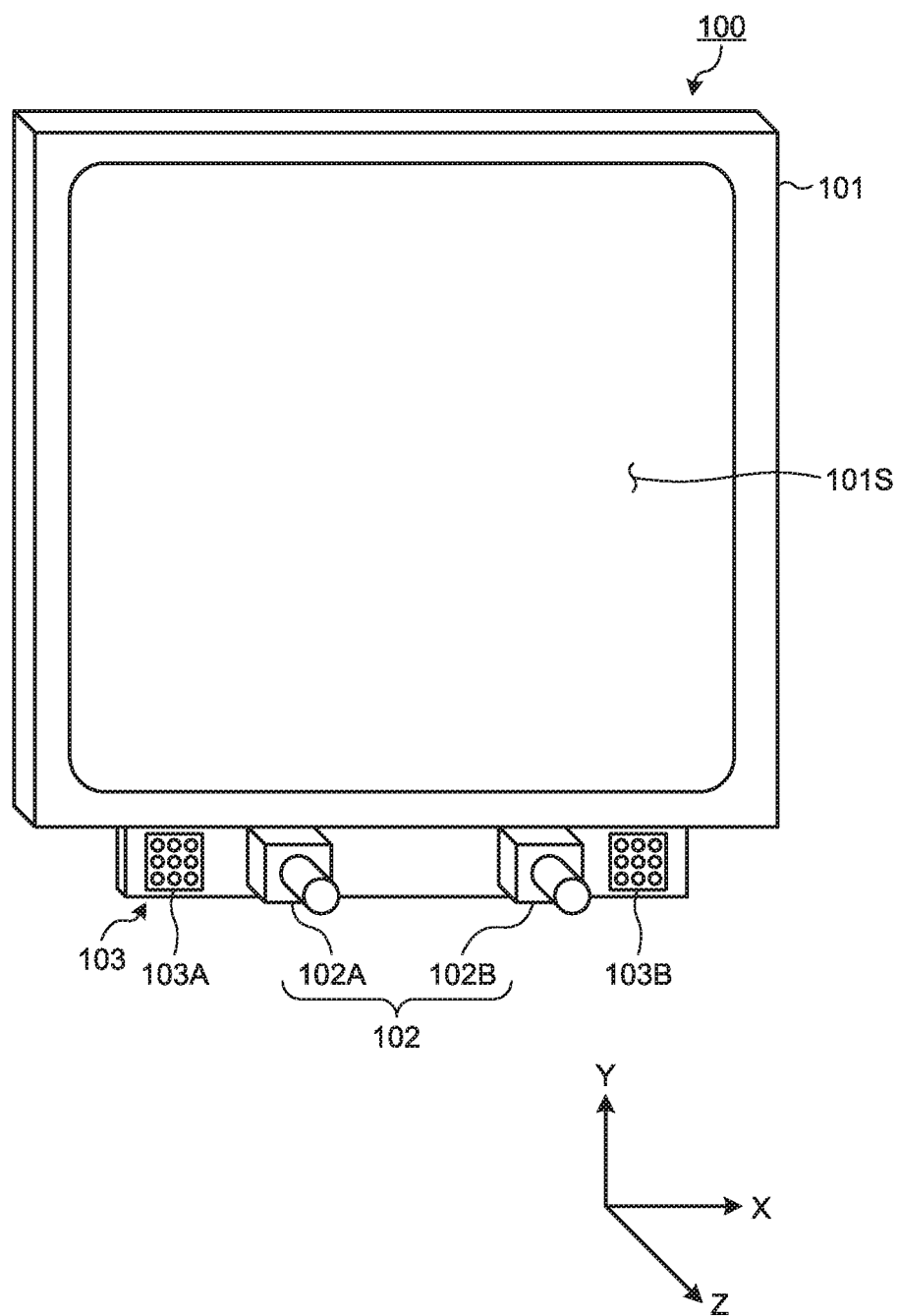
FIG. 1 is a perspective view schematically illustrating an example of a line-of-sight detection device according to a present embodiment.

FIG. 1 is a perspective view schematically illustrating an example of a line-of-sight detection device 100 according to the present embodiment. As illustrated in FIG. 1, the line-of-sight detection device 100 includes a display device 101, a stereo camera device 102, and a lighting device 103.

The display device 101 includes a flat panel display, such as a liquid crystal display (LCD) or an organic electroluminescence display (OLED).

In the present embodiment, a display screen 101S of the display device 101 is substantially parallel to the XY plane. The X-axis direction is a horizontal direction of the display screen 101S, the Y-axis direction is a vertical direction of the display screen 101S, and the Z-axis direction is a depth direction perpendicular to the display screen 101S. Further, a rightward direction with respect to the display screen 101S is a positive X direction, the leftward direction is a negative X direction, an upward direction is a positive Y direction, a downward direction is a negative Y direction, a forward direction is a positive Z direction, and a rearward direction is a negative Z direction.

The stereo camera device 102 includes a first camera 102A and a second camera 102B. The stereo camera device 102 is arranged below the display screen 101S of the display device 101. The first camera 102A and the second camera 102B are arranged in the X-axis direction. The first camera 102A is arranged on the negative X side relative to the second camera 102B. Each of the first camera 102A and the second camera 102B includes an infrared camera, and includes, for example, an optical system capable of transmitting near-infrared light with a wavelength of 850 [nm] and an imaging element capable of receiving the near-infrared light.

The lighting device 103 includes a first light source 103A and a second light source 103B. The lighting device 103 is arranged below the display screen 101S of the display device 101. The first light source 103A and the second light source 103B are arranged in the X-axis direction. The first light source 103A is arranged on the negative X side relative to the first camera 102A. The second light source 103B is arranged on the positive X side relative to the second camera 102B. Each of the first light source 103A and the second light source 103B includes a light emitting diode (LED) light source and capable of emitting, for example, near-infrared light with a wavelength of 850 [nm]. Meanwhile, the first light source 103A and the second light source 103B may be arranged between the first camera 102A and the second camera 102B.

Figure 2:
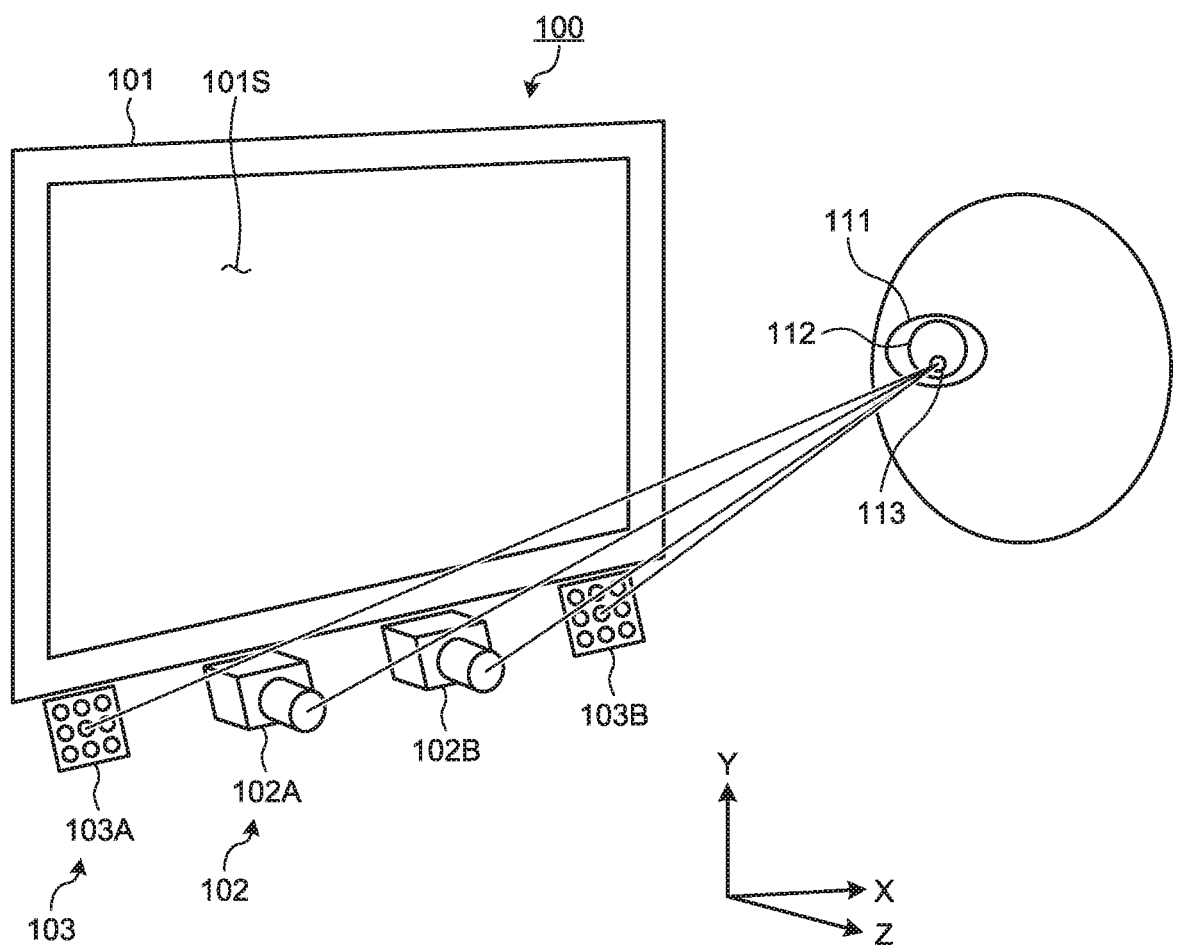
FIG. 2 is a diagram schematically illustrating a positional relationship among a display device, a stereo camera device, a lighting device, and an eyeball of a subject according to the present embodiment.

FIG. 2 is a diagram schematically illustrating a positional relationship among the display device 101, the stereo camera device 102, the lighting device 103, and an eyeball 111 of a subject according to the present embodiment.

The lighting device 103 emits near-infrared light as detection light and irradiates the eyeball 111 of the subject. The stereo camera device 102 captures an image of the eyeball 111 with the second camera 102B when the eyeball 111 is irradiated with the detection light emitted from the first light source 103A, and captures an image of the eyeball 111 with the first camera 102A when the eyeball 111 is irradiated with the detection light emitted from the second light source 103B.

At least one of the first camera 102A and the second camera 102B outputs a frame synchronous signal. The first light source 103A and the second light source 103B emit the detection light based on the frame synchronous signal. The first camera 102A acquires image data of the eyeball 111 when the eyeball 111 is irradiated with the detection light emitted from the second light source 103B. The second camera 102B acquires image data of the eyeball 111 when the eyeball 111 is irradiated with the detection light emitted from the first light source 103A.

When the eyeball 111 is irradiated with the detection light, a part of the detection light is reflected by a pupil 112, and light from the pupil 112 enters the stereo camera device 102. Further, when the eyeball 111 is irradiated with the detection light, a corneal reflection image 113 that is a virtual image of a cornea is formed on the eyeball 111, and light from the corneal reflection image 113 enters the stereo camera device 102.

By appropriately setting relative positions of the first camera 102A, the second camera 102B, the first light source 103A, and the second light source 103B, intensity of the light that enters the stereo camera device 102 from the pupil 112 decreases and intensity of the light that enters the stereo camera device 102 from the corneal reflection image 113 increases. In other words, an image of the pupil 112 acquired by the stereo camera device 102 has low luminance and an image of the corneal reflection image 113 has high luminance. The stereo camera device 102 is able to detect a position of the pupil 112 and a position of the corneal reflection image 113 on the basis of the luminance of the acquired images.

Figure 3:
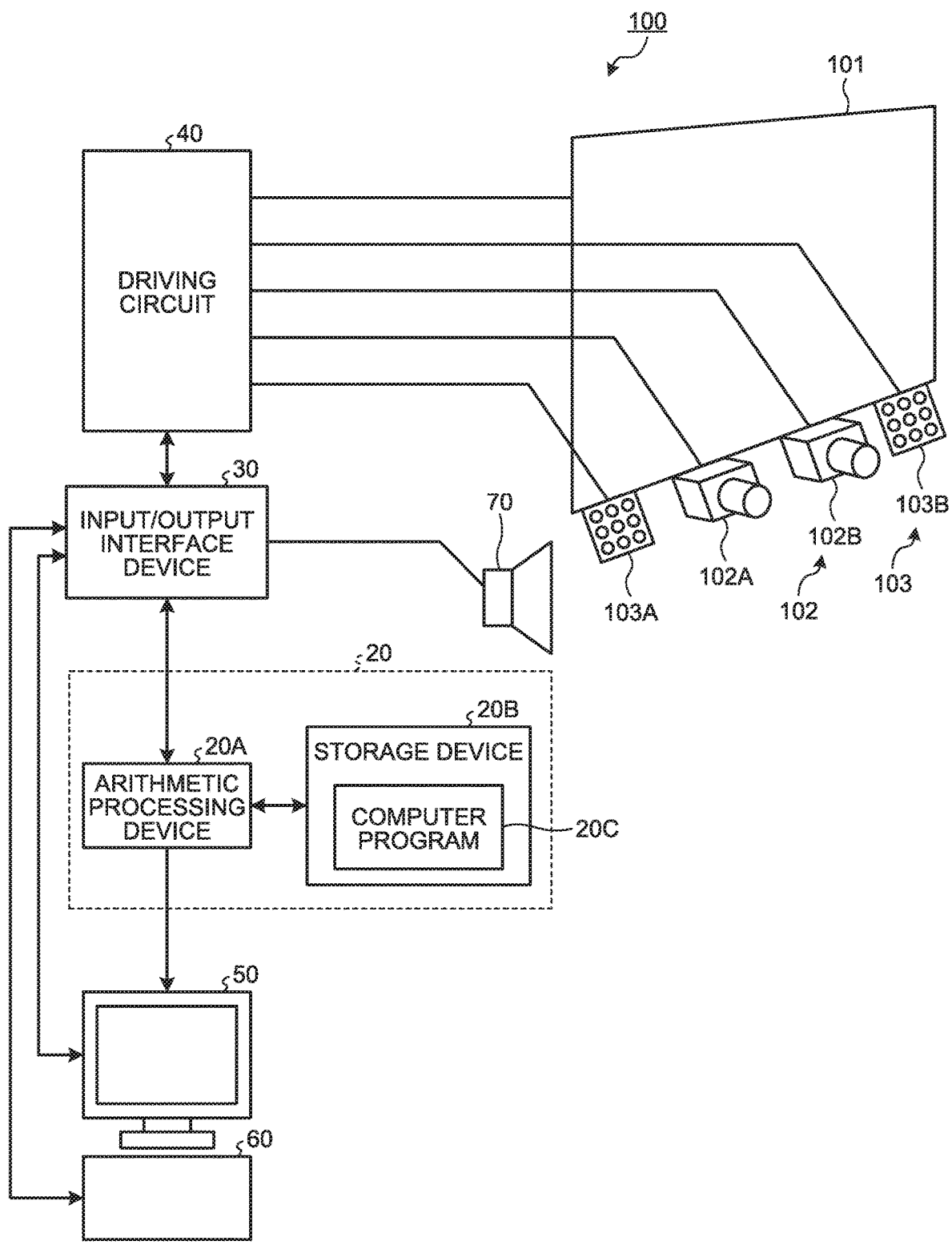
FIG. 3 is a diagram illustrating an example of a hardware configuration of the line-of-sight detection device according to the present embodiment.

FIG. 3 is a diagram illustrating an example of a hardware configuration of the line-of-sight detection device 100 according to the present embodiment. As illustrated in FIG. 3, the line-of-sight detection device 100 includes the display device 101, the stereo camera device 102, the lighting device 103, a computer system 20, an input/output interface device 30, a driving circuit 40, an output device 50, an input device 60, and a voice output device 70. The computer system 20 includes an arithmetic processing device 20A and a storage device 20B.

The computer system 20, the driving circuit 40, the output device 50, the input device 60, and the voice output device 70 perform data communication via the input/output interface device 30.

The arithmetic processing device 20A includes a microprocessor, such as a central processing unit (CPU). The storage device 20B includes a memory or a storage, such as a read only memory (ROM) and a random access memory (RAM). The arithmetic processing device 20A performs arithmetic processing in accordance with a computer program 20C stored in the storage device 20B.

The driving circuit 40 generates a driving signal and outputs the driving signal to the display device 101, the stereo camera device 102, and the lighting device 103. Further, the driving circuit 40 supplies image data of the eyeball 111 acquired by the stereo camera device 102 to the computer system 20 via the input/output interface device 30.

The output device 50 includes a display device, such as a flat panel display. Meanwhile, the output device 50 may include a printing device. The input device 60 generates input data by being operated. The input device 60 includes a keyboard or a mouse for the computer system. Meanwhile, the input device 60 may include a touch sensor that is provided on a display screen of the output device 50 that is the display device. The voice output device 70 includes a speaker and outputs voice for alerting the subject, for example.

In the present embodiment, the display device 101 and the computer system 20 are separate devices. Meanwhile, the display device 101 and the computer system 20 may be integrated with each other. For example, if the line-of-sight detection device 100 includes a tablet personal computer, the computer system 20, the input/output interface device 30, the driving circuit 40, and the display device 101 may be mounted on the tablet personal computer.

Figure 4:
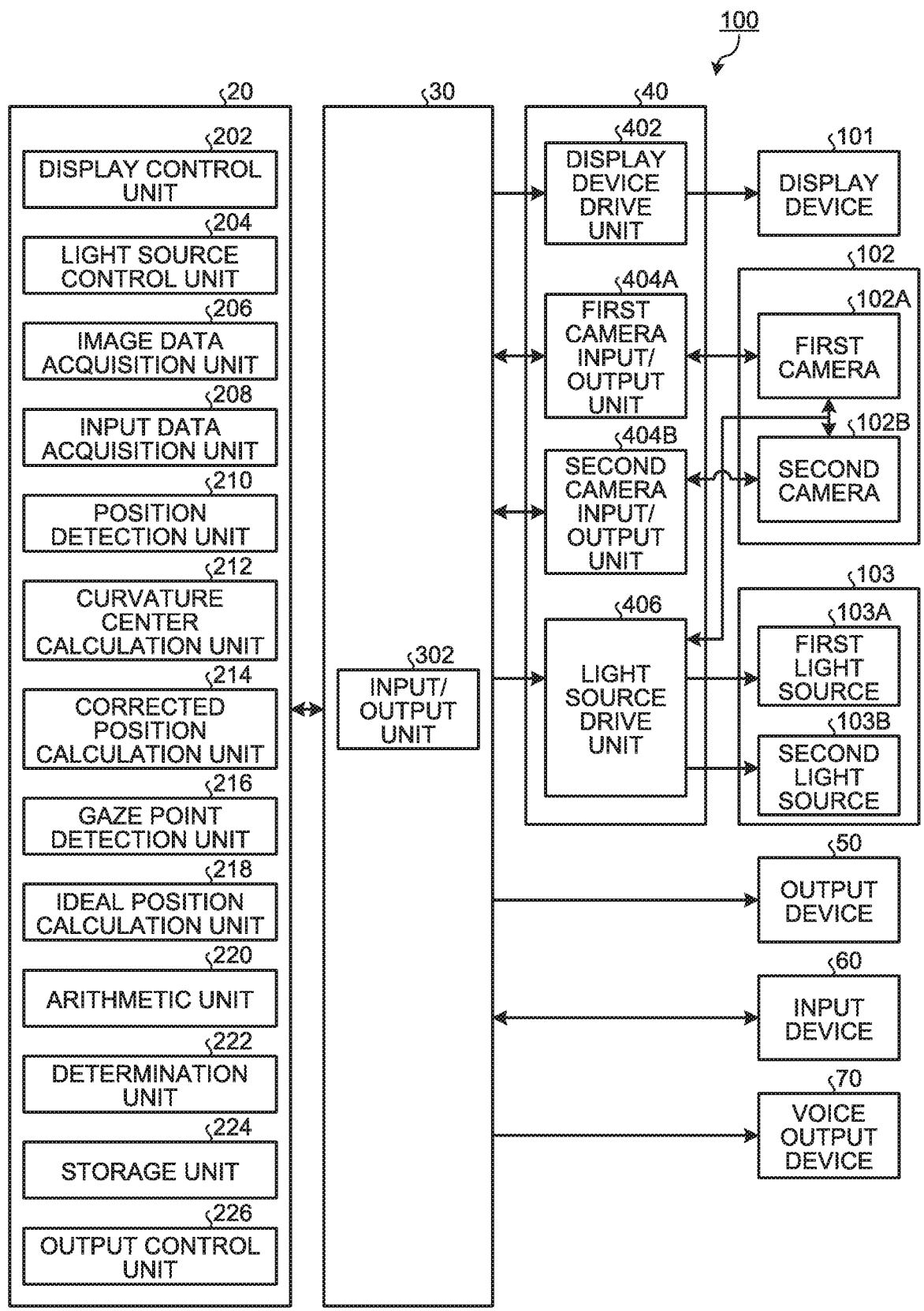
FIG. 4 is a functional block diagram illustrating an example of the line-of-sight detection device according to the present embodiment.

FIG. 4 is a functional block diagram illustrating an example of the line-of-sight detection device 100 according to the present embodiment. As illustrated in FIG. 4, the input/output interface device 30 includes an input/output unit 302. The driving circuit 40 includes a display device drive unit 402 that generates a driving signal for driving the display device 101 and outputs the driving signal to the display device 101, a first camera input/output unit 404A that generates a driving signal for driving the first camera 102A and outputs the driving signal to the first camera 102A, a second camera input/output unit 404B that generates a driving signal for driving the second camera 102B and outputs the driving signal to the second camera 102B, and a light source drive unit 406 that generates driving signals for driving the first light source 103A and the second light source 103B and outputs the driving signals to the first light source 103A and the second light source 103B. Further, the first camera input/output unit 404A supplies the image data of the eyeball 111 acquired by the first camera 102A to the computer system 20 via the input/output unit 302. The second camera input/output unit 404B supplies the image data of the eyeball 111 acquired by the second camera 102B to the computer system 20 via the input/output unit 302.

The computer system 20 controls the line-of-sight detection device 100. The computer system 20 includes a display control unit 202, a light source control unit 204, an image data acquisition unit 206, an input data acquisition unit 208, a position detection unit 210, a curvature center calculation unit 212, a corrected position calculation unit 214, a gaze point detection unit 216, an ideal position calculation unit 218, an arithmetic unit 220, a determination unit 222, a storage unit 224, and an output control unit 226. Functions of the computer system 20 are implemented by the arithmetic processing device 20A and the storage device 20B.

The display control unit 202 causes the display screen 101S of the display device 101 to display an image to be presented to the subject. The display control unit 202 is able to display an image at a single point on the display screen 101S, for example.

The light source control unit 204 controls the light source drive unit 406 to thereby control operation states of the first light source 103A and the second light source 103B. The light source control unit 204 controls the first light source 103A and the second light source 103B such that the first light source 103A and the second light source 103B emit the detection light at different timings.

The image data acquisition unit 206 acquires the image data of the eyeball 111 of the subject acquired by the stereo camera device 102 including the first camera 102A and the second camera 102B, from the stereo camera device 102 via the input/output unit 302.

The input data acquisition unit 208 acquires input data generated through operation on the input device 60, from the input device 60 via the input/output unit 302.

The position detection unit 210 detects a position of a pupil center on the basis of the image data of the eyeball 111 acquired by the image data acquisition unit 206. Further, the position detection unit 210 detects a position of a corneal reflection center on the basis of the image data of the eyeball 111 acquired by the image data acquisition unit 206. The pupil center is a center of the pupil 112. The corneal reflection center is a center of the corneal reflection image 113. The position detection unit 210 detects the position of the pupil center and the position of the corneal reflection center for each of the right and left eyeballs 111 of the subject.

The curvature center calculation unit 212 calculates the position of the corneal curvature on the basis of the image data of the eyeball 111 acquired by the image data acquisition unit 206.

The corrected position calculation unit 214 corrects the position of the corneal curvature center on the basis of a distance between the center of the pupil 112 detected by the position detection unit 210 and the corneal curvature center calculated by the curvature center calculation unit 212, and calculates a position of the corrected corneal curvature center for each of the right and left eyeballs.

The gaze point detection unit 216 detects a position of a gaze point of the subject on the basis of the image data of the eyeball 111 acquired by the image data acquisition unit 206. In the present embodiment, the position of the gaze point is a position of an intersection between a line-of-sight vector of the subject defined in the three-dimensional global coordinate system and the display screen 101S of the display device 101. The gaze point detection unit 216 detects the line-of-sight vector that is a line-of-sight direction of each of the right and left eyeballs 111 of the subject, on the basis of the position of the pupil center and the position of the corneal curvature center acquired from the image data of the eyeball 111. In other words, the gaze point detection unit 216 also serves as a line-of-sight detection unit that detects the line-of-sight direction of each of the right and left eyeballs 111 of the subject. After detecting the line-of-sight vector of each of the right and left eyeballs 111 of the subject, the gaze point detection unit 216 detects the position of the gaze point indicating the intersection between the line-of-sight vector and the display screen 101S.

The ideal position calculation unit 218 calculates a position of an ideal corneal curvature center of each of the right and left eyeballs, on the basis of a position of an image displayed at a single point on the display screen 101S and the position of the center of the pupil 112.

The arithmetic unit 220 calculates a positional difference that is a difference between the position of the corrected corneal curvature center calculated by the corrected position calculation unit 214 and the position of the ideal corneal curvature center calculated by the ideal position calculation unit 218, for each of the right and left eyeballs. Further, the arithmetic unit 220 calculates a right-left difference that is a difference between the positional differences of the right and left eyeballs.

The determination unit 222 determines whether the gaze point of each of the right and left eyeballs, which is detected by the gaze point detection unit 216, is valid on the basis of a magnitude of the right-left difference.

The storage unit 224 stores therein a line-of-sight detection program that causes a computer to perform the following processes: a process of displaying an image at a single point on the display screen 101S of the display device 101; a process of irradiating the right and left eyeballs of the subject with near-infrared light from a light source; a process of acquiring image data of the right and left eyeballs of the subject irradiated with the near-infrared light; a process of detecting a position of the pupil center indicating the center of the pupil 112 and a position of the corneal reflection center indicating the center of the corneal reflection image 113 for each of the right and left eyeballs; a process of calculating the position of the corneal curvature center of each of the right and left eyeballs on the basis of a virtual line connecting the light source and the corneal reflection center and a virtual line connecting the image and the pupil center; a process of correcting the position of the corneal curvature center on the basis of a distance between the pupil center and the corneal curvature center and calculating a position of the corrected corneal curvature center for each of the right and left eyeballs; a process of detecting a gaze point of each of the right and left eyeballs from the position of the pupil center and the position of the corrected corneal curvature center; a process of calculating a position of an ideal corneal curvature center of each of the right and left eyeballs from the position of the image displayed at the single point on the display screen 101S and the position of the pupil center; a process of calculating the positional difference that is a difference between the position of the corrected corneal curvature center and the position of the ideal corneal curvature center for each of the right and left eyeballs; and a process of determining whether the gaze point of each of the right and left eyeballs detected by the gaze point detection unit 216 is valid on the basis of a magnitude of the right-left difference that is a difference between the positional differences of the right and left eyeballs.

The output control unit 226 outputs data to at least one of the display device 101, the output device 50, and the voice output device 70. In the present embodiment, the output control unit 226 displays an image at a single point on the display screen 101S. Further, the output control unit 226 the causes the display screen 101S or the output device 50 to display the position of the gaze point of each of the right and left eyeballs 111 of the subject.

An overview of processes performed by the curvature center calculation unit 212 according to the present embodiment will be described below. The curvature center calculation unit 212 calculates the position of the corneal curvature center of the eyeball 111 on the basis of the image data of the eyeball 111.

Figure 5:
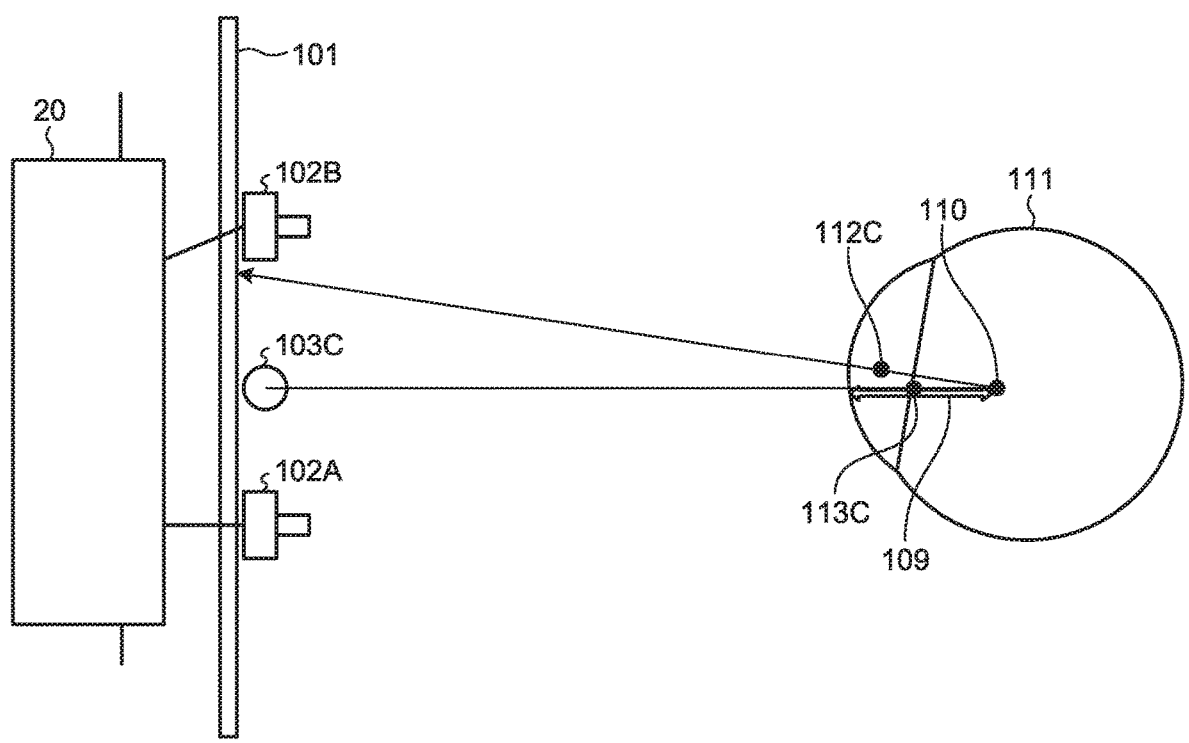
FIG. 5 is a schematic diagram for explaining a method of calculating a position of a corneal curvature center according to the present embodiment.
Figure 6:
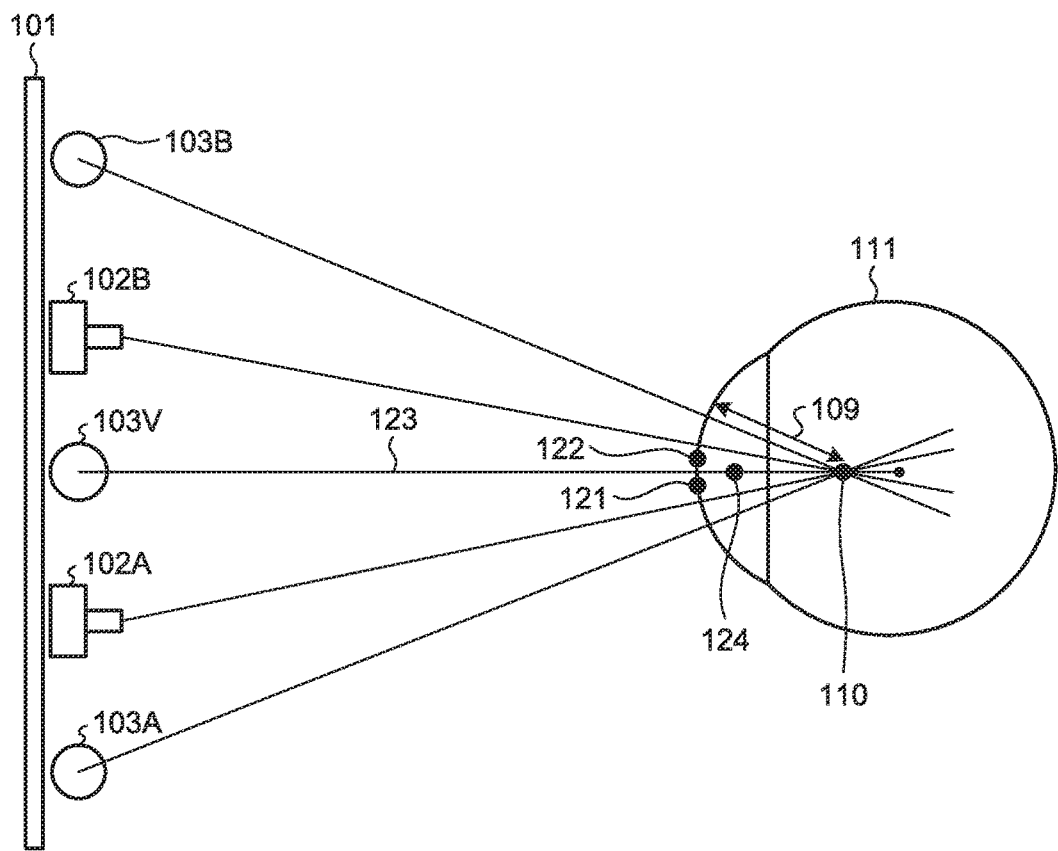
FIG. 6 is a schematic diagram for explaining the method of calculating the position of the corneal curvature center according to the present embodiment.

FIG. 5 and FIG. 6 are schematic diagrams for explaining a method of calculating a position of a corneal curvature center 110 according to the present embodiment. FIG. 5 illustrates an example in which the eyeball 111 is irradiated with a single light source 103C. FIG. 6 illustrates an example in which the eyeball 111 is irradiated with the first light source 103A and the second light source 103B.

First, the example illustrated in FIG. 5 will be described. The light source 103C is arranged between the first camera 102A and the second camera 102B. A pupil center 112C is the center of the pupil 112. A corneal reflection center 113C is the center of the corneal reflection image 113. In FIG. 5, the pupil center 112C indicates the pupil center in a case where the eyeball 111 is irradiated with the single light source 103C. The corneal reflection center 113C indicates the corneal reflection center in a case where the eyeball 111 is irradiated with the single light source 103C.

The corneal reflection center 113C is located on a straight line connecting the light source 103C and the corneal curvature center 110. The corneal reflection center 113C is positioned at a middle point between the corneal surface and the corneal curvature center 110. A corneal curvature radius 109 is a distance between the corneal surface and the corneal curvature center 110.

The position of the corneal reflection center 113C is detected by the stereo camera device 102. The corneal curvature center 110 is located on a straight line connecting the light source 103C and the corneal reflection center 113C. The curvature center calculation unit 212 calculates, as the position of the corneal curvature center 110, a position at which a distance from the corneal reflection center 113C corresponds to a predetermined value on the straight line. The predetermined value is a value that is determined in advance from a general corneal curvature radius value or the like, and stored in the storage unit 224.

Next, the example illustrated in FIG. 6 will be described. In the present embodiment, the first camera 102A and the second light source 103B are arranged at bilaterally symmetric positions and the second camera 102B and the first light source 103A are arranged at bilaterally symmetric positions, with respect to a straight line that passes a middle position between the first camera 102A and the second camera 102B. It is possible to assume that a virtual light source 103V is present at the middle position between the first camera 102A and the second camera 102B.

A corneal reflection center 121 indicates a corneal reflection center in an image that is obtained by imaging the eyeball 111 by the second camera 102B. A corneal reflection center 122 indicates a corneal reflection center in an image that is obtained by imaging the eyeball 111 by the first camera 102A. A corneal reflection center 124 indicates a corneal reflection center corresponding to the virtual light source 103V.

The position of the corneal reflection center 124 is calculated based on the position of the corneal reflection center 121 and the position of the corneal reflection center 122 acquired by the stereo camera device 102. The stereo camera device 102 detects the position of the corneal reflection center 121 and the position of the corneal reflection center 122 in the three-dimensional local coordinate system defined by the stereo camera device 102. Camera calibration based on a stereo calibration method is performed in advance on the stereo camera device 102, and a conversion parameter for converting the three-dimensional local coordinate system of the stereo camera device 102 to the three-dimensional global coordinate system is calculated. The conversion parameter is stored in the storage unit 224.

The curvature center calculation unit 212 converts the position of the corneal reflection center 121 and the position of the corneal reflection center 122 acquired by the stereo camera device 102 to positions in the three-dimensional global coordinate system by using the conversion parameter. The curvature center calculation unit 212 calculates the position of the corneal reflection center 124 in the three-dimensional global coordinate system based on the position of the corneal reflection center 121 and the position of the corneal reflection center 122 defined by the three-dimensional global coordinate system.

The corneal curvature center 110 is located on a straight line 123 connecting the virtual light source 103V and the corneal reflection center 124. The curvature center calculation unit 212 calculates, as the position of the corneal curvature center 110, a position at which a distance from the corneal reflection center 124 corresponds to a predetermined value on the straight line 123. The predetermined value is a value that is determined in advance from a general corneal curvature radius value or the like, and stored in the storage unit 224.

As described above, even when two light sources are provided, the corneal curvature center 110 is calculated by the same method as the method that is used when a single light source is provided.

The corneal curvature radius 109 is a distance between the corneal surface and the corneal curvature center 110. Therefore, the corneal curvature radius 109 is calculated by calculating the position of the corneal surface and the position of the corneal curvature center 110.

Line-of-Sight Detection Method

Figure 7:
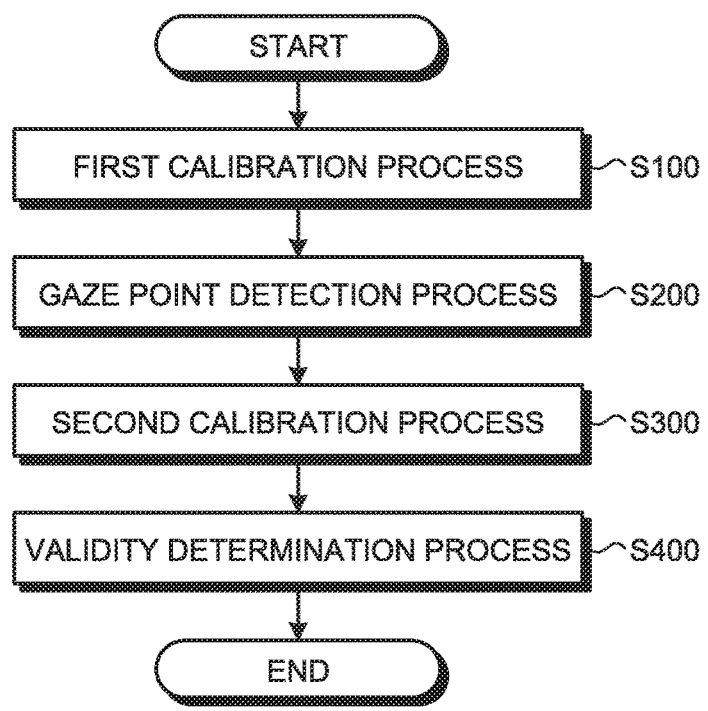
FIG. 7 is a flowchart illustrating an example of a line-of-sight detection method according to the present embodiment.

An example of the line-of-sight detection method according to the present embodiment will be described below. FIG. 7 is a flowchart illustrating an example of the line-of-sight detection method according to the present embodiment. In the present embodiment, a first calibration process including a process of calculating the position of the corneal curvature center 110 and a process of calculating distance data between the pupil center 112C and the corneal curvature center 110 (Step S100), a gaze point detection process (Step S200), a second calibration process including a process of calculating the position of the ideal corneal curvature center 110 (Step S300), and a validity determination process of determining whether the gaze point of each of the right and left eyeballs detected at Step S200 is valid on the basis of the magnitude of the right-left difference that is a difference between the positional differences of the right and left eyeballs (Step S400) are performed.

First Calibration Process

Figure 8:
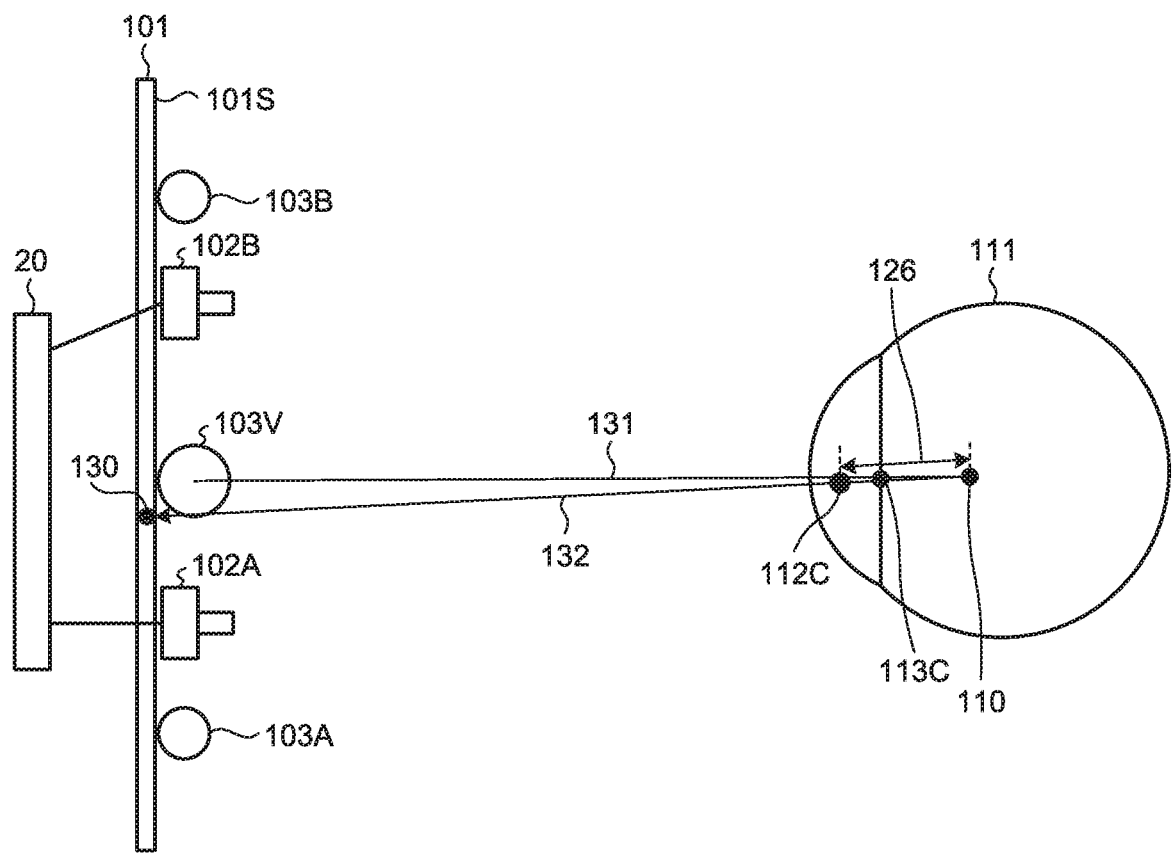
FIG. 8 is a schematic diagram for explaining an example a first calibration process according to the present embodiment.

The first calibration process (Step S100) will be described. FIG. 8 is a schematic diagram for explaining an example of the first calibration process according to the present embodiment. The first calibration process includes calculation of the position of the corneal curvature center 110 and calculation of a distance 126 between the pupil center 112C and the corneal curvature center 110.

A target position 130 of gaze of the subject is set. The target position 130 is defined in the three-dimensional global coordinate system. In the present embodiment, the target position 130 is set to a central position on the display screen 101S of the display device 101, for example. Meanwhile, the target position 130 may be set to an edge position of the display screen 101S.

The display control unit 202 displays a target image at the set target position 130. Accordingly, the subject is able to easily gaze at the target position 130.

A straight line 131 is a straight line that connects the virtual light source 103V and the corneal reflection center 113C. A straight line 132 is a straight line that connects the target position 130 and the pupil center 112C. The corneal curvature center 110 is an intersection between the straight line 131 and the straight line 132. The curvature center calculation unit 212 is able to calculate the position of the corneal curvature center 110 based on the position of the virtual light source 103V, the position of the target position 130, the position of the pupil center 112C, and the position of the corneal reflection center 113C.

Figure 9:
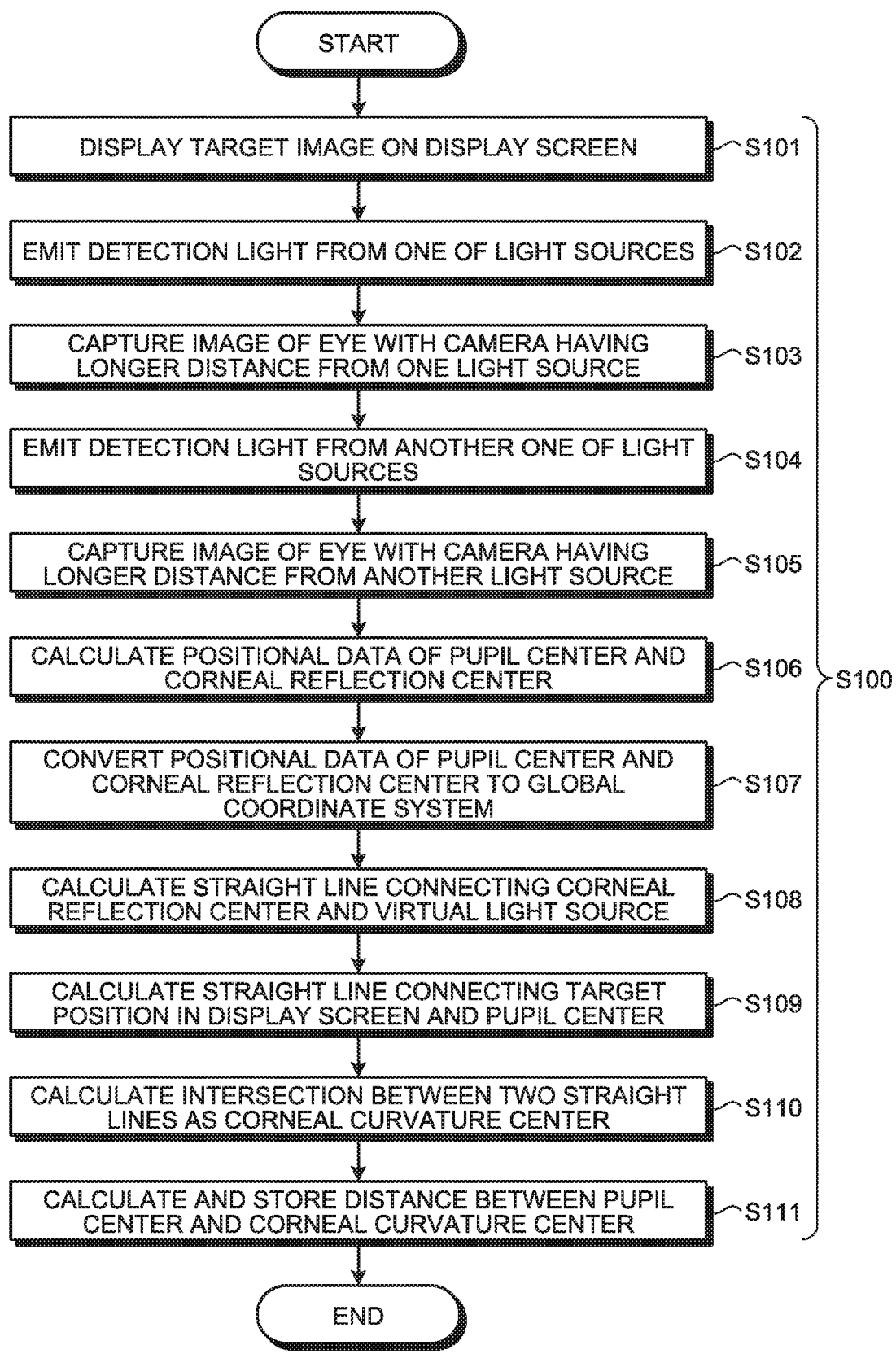
FIG. 9 is a flowchart illustrating an example of the first calibration process according to the present embodiment.

FIG. 9 is a flowchart illustrating an example of the first calibration process (Step S100) according to the present embodiment. The display control unit 202 causes the display screen 101S of the display device 101 to display a target image (Step S101). The subject is able to gaze at the target position 130 by gazing at the target image.

Subsequently, the light source control unit 204 causes the light source drive unit 406 to emit the detection light from one of the first light source 103A and the second light source 103B (Step S102). The stereo camera device 102 captures an image of the eye of the subject with the camera having a longer distance from the light source that has emitted the detection light among the first camera 102A and the second camera 102B (Step S103).

Subsequently, the light source control unit 204 causes the light source drive unit 406 to emit the detection light from the other one of the first light source 103A and the second light source 103B (Step S104). The stereo camera device 102 captures an image of the eye of the subject with the camera having a longer distance from the light source that has emitted the detection light among the first camera 102A and the second camera 102B (Step S105).

The stereo camera device 102 detects the pupil 112 as a dark portion, and the stereo camera device 102 detects the corneal reflection image 113 as a bright portion. In other words, the image of the pupil 112 obtained by the stereo camera device 102 has low luminance, and the image of the corneal reflection image 113 has high luminance. The position detection unit 210 is able to detect the position of the pupil 112 and the position of the corneal reflection image 113 on the basis of the luminance of the obtained images. Further, the position detection unit 210 calculates the position of the pupil center 112C on the basis of the image data of the pupil 112. Furthermore, the position detection unit 210 calculates the position of the corneal reflection center 113C on the basis of the image data of the corneal reflection image 113 (Step S106).

The positions detected by the stereo camera device 102 are positions defined in the three-dimensional local coordinate system. The position detection unit 210 performs, by using the conversion parameter stored in the storage unit 224, coordinate transformation on the position of the pupil center 112C and the position of the corneal reflection center 113C detected by the stereo camera device 102, and calculates the position of the pupil center 112C and the position of the corneal reflection center 113C defined in the three-dimensional global coordinate system (Step S107).

The curvature center calculation unit 212 calculates the straight line 131 that connects the corneal reflection center 113C defined in the global coordinate system and the virtual light source 103V (Step S108).

Subsequently, the curvature center calculation unit 212 calculates the straight line 132 that connects the target position 130 defined in the display screen 101S of the display device 101 and the pupil center 112C (Step S109). The curvature center calculation unit 212 obtains an intersection between the straight line 131 calculated at Step S108 and the straight line 132 calculated at Step S109, and sets the intersection as the corneal curvature center 110 (Step S110).

The curvature center calculation unit 212 calculates the distance 126 between the pupil center 112C and the corneal curvature center 110, and stores the distance 126 in the storage unit 224 (Step S111). The stored distance is used to calculate the corneal curvature center 110 in the gaze point detection at Step S200.

Gaze Point Detection Process

Next, the gaze point detection process (Step S200) will be described. The gaze point detection process is performed after the first calibration process. The gaze point detection unit 216 calculates the line-of-sight vector and the position of the gaze point of the subject on the basis of the image data of the eyeball 111.

Figure 10:
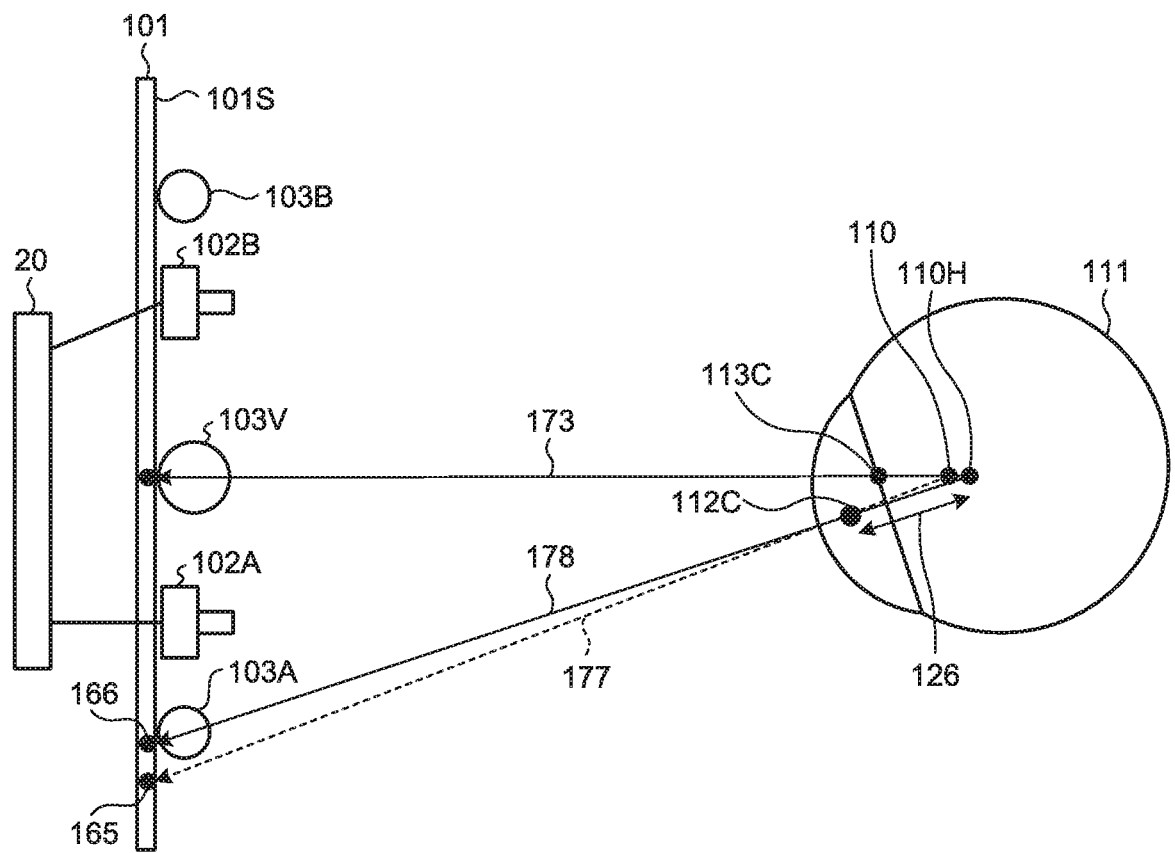
FIG. 10 is a schematic diagram for explaining an example a gaze point detection process according to the present embodiment.

FIG. 10 is a schematic diagram for explaining an example the gaze point detection process according to the present embodiment. The gaze point detection process includes correction of the position of the corneal curvature center 110 by using the distance 126 between the pupil center 112C and the corneal curvature center 110 obtained in the first calibration process (Step S100), and calculation of the gaze point by using the position of the corrected corneal curvature center 110.

In FIG. 10, a gaze point 165 indicates a gaze point obtained from the corneal curvature center 110 that is calculated using a general curvature radius value. A gaze point 166 indicates a gaze point obtained from a corneal curvature center 110H that is calculated using the distance 126 obtained in the first calibration process.

The pupil center 112C indicates the pupil center calculated in the first calibration process, and the corneal reflection center 113C indicates the corneal reflection center calculated in the first calibration process.

A straight line 173 is a straight line that connects the virtual light source 103V and the corneal reflection center 113C. The corneal curvature center 110 is a position of a corneal curvature center that is calculated from a general curvature radius value.

The distance 126 is a distance between the pupil center 112C and the corneal curvature center 110 calculated in the first calibration process.

The corneal curvature center 110H indicates a position of the corrected corneal curvature center that is obtained by correcting the corneal curvature center 110 by using the distance 126.

The corneal curvature center 110H is obtained based on the fact that the corneal curvature center 110 is located on the straight line 173 and the distance between the pupil center 112C and the corneal curvature center 110 is the distance 126. Accordingly, a line of sight 177 that is calculated using a general curvature radius value is corrected to a line of sight 178. Further, the gaze point on the display screen 101S of the display device 101 is corrected from the gaze point 165 to the gaze point 166.

Figure 11:
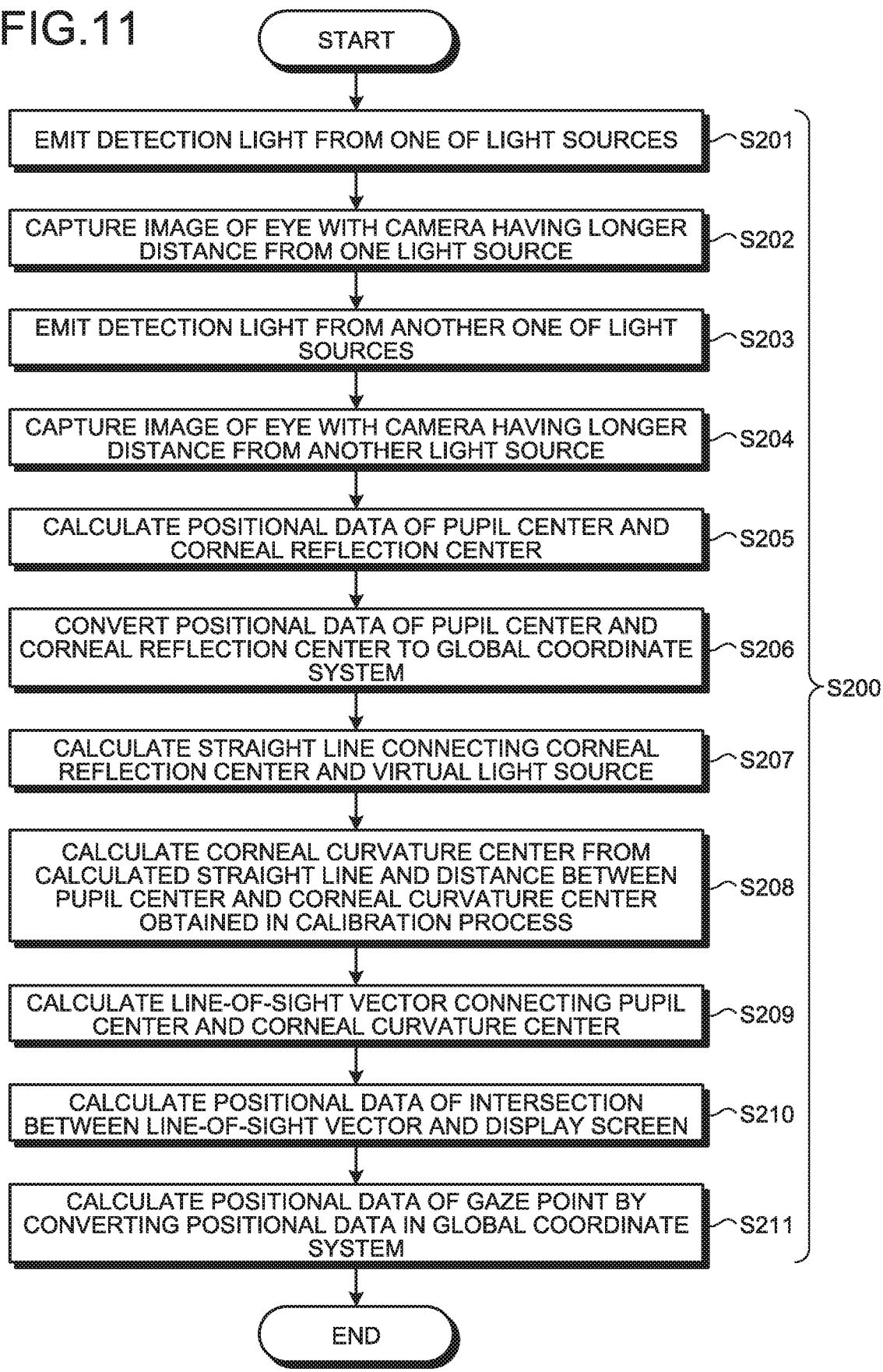
FIG. 11 is a flowchart illustrating an example of the gaze point detection process according to the present embodiment.

FIG. 11 is a flowchart illustrating an example of the gaze point detection process (Step S200) according to the present embodiment. Meanwhile, processes from Step S201 to Step S207 illustrated in FIG. 11 are the same as the processes from Step S102 to Step S108 illustrated in FIG. 9, and therefore explanation thereof will be omitted.

The corrected position calculation unit 214 calculates, as the corneal curvature center 110H that is a corrected corneal curvature center, a position which is located on the straight line 173 calculated at Step S207 and for which a distance from the pupil center 112C is equal to the distance 126 that is obtained in the calibration process (Step S208).

The gaze point detection unit 216 calculates a line-of-sight vector that connects the pupil center 112C and the corneal curvature center 110H (Step S209). The line-of-sight vector indicates a line-of-sight direction viewed by the subject. The gaze point detection unit 216 calculates a position of an intersection between the line-of-sight vector and the display screen 101S of the display device 101 (Step S210). The position of the intersection between the line-of-sight vector and the display screen 101S of the display device 101 is the position of the gaze point of the subject in the display screen 101S defined in the three-dimensional global coordinate system.

The gaze point detection unit 216 converts the position of the gaze point defined in the three-dimensional global coordinate system to a position in the display screen 101S of the display device 101 defined in a two-dimensional coordinate system (Step S211). Consequently, the position of the gaze point on the display screen 101S of the display device 101 viewed by the subject is calculated.

Second Calibration Process

Figure 12:
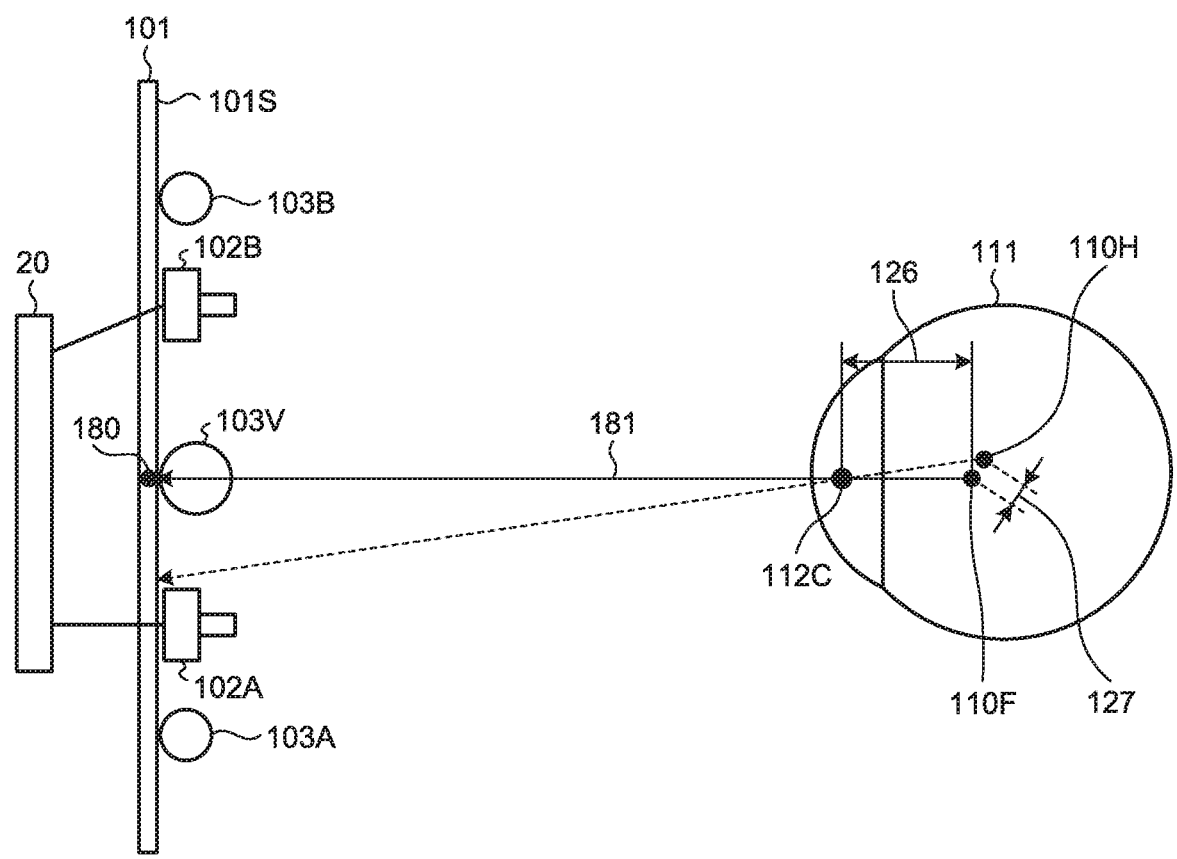
FIG. 12 is a schematic diagram for explaining an example of a second calibration process according to the present embodiment.

Next, the second calibration process (Step S300) will be described. FIG. 12 is a schematic diagram for explaining an example of the second calibration process according to the present embodiment. The second calibration process includes calculation of a position of an ideal corneal curvature center 110F of each of the right and left eyeballs.

As illustrated in FIG. 12, in the second calibration process, a target position 180 of gaze of the subject. The target position 180 is defined in the three-dimensional global coordinate system. In the present embodiment, the target position 180 is set at a central position of the display screen 101S of the display device 101, for example. Meanwhile, the target position 180 may be set at an edge position of the display screen 101S. The display control unit 202 displays a target image at the set target position 180. Accordingly, the subject is able to easily gaze at the target position 180.

The pupil center 112C is the pupil center calculated in the first calibration process. A straight line 181 is a straight line that connects the virtual light source 103V and the pupil center 112C. The distance 126 is the distance between the pupil center 112C and the corneal curvature center 110F calculated in the first calibration process.

The ideal corneal curvature center 110F is set at a position that is located on the straight line 181 and that is separated by the distance 126 from the pupil center 112C. The ideal position calculation unit 218 is able to calculate the position of the ideal corneal curvature center 110F on the basis of the position of the target position 180, the position of the pupil center 112C, and the data of the distance 126 between the pupil center 112C and the corneal curvature center 110. A positional difference 127 is a distance between the ideal corneal curvature center 110F and the above-described corrected corneal curvature center 110H.

Figure 13:
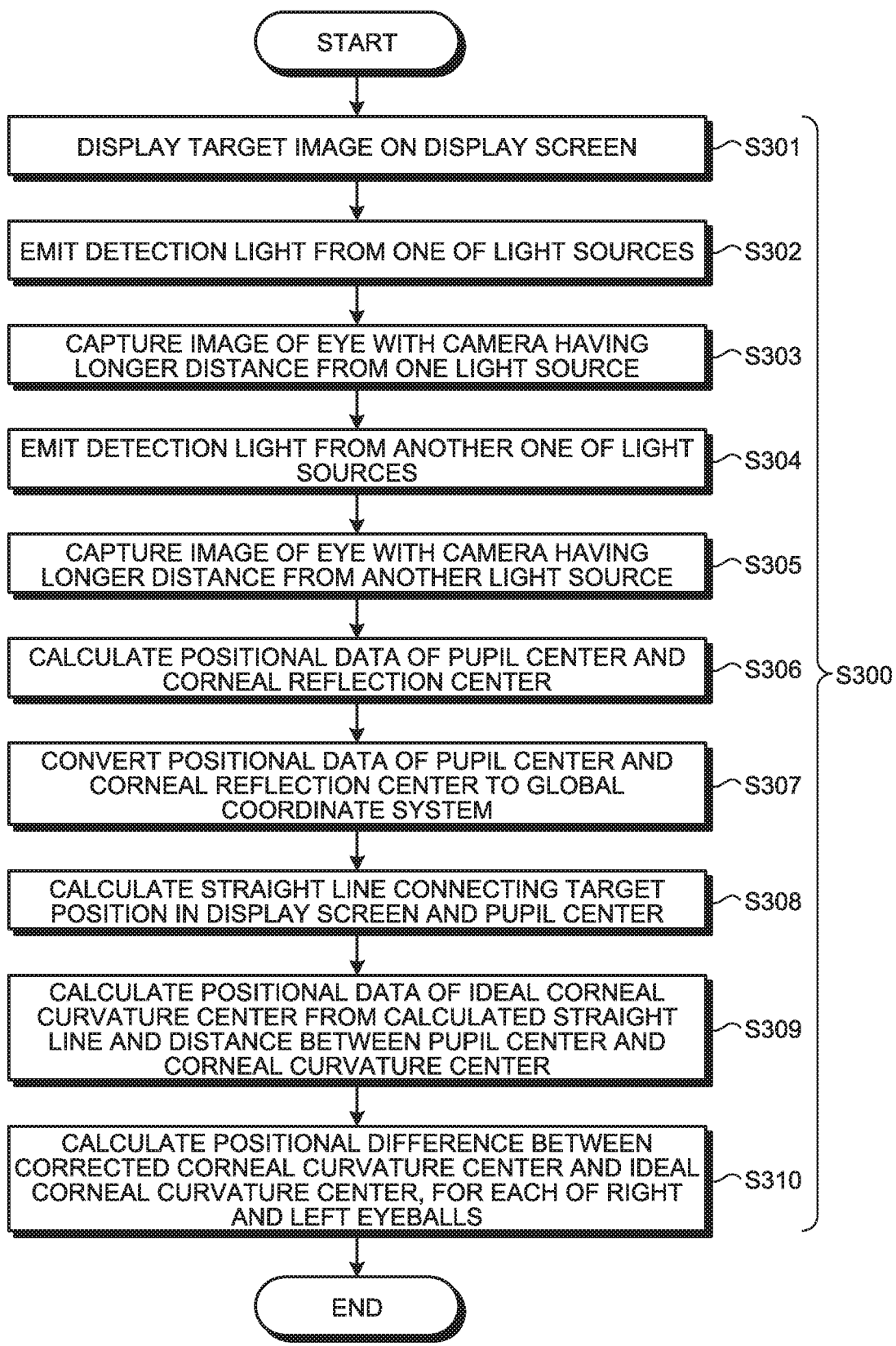
FIG. 13 is a flowchart illustrating an example of the second calibration process according to the present embodiment.

FIG. 13 is a flowchart illustrating an example of the second calibration process (S300) according to the present embodiment. Meanwhile, processes from Step S301 to Step S307 illustrated in FIG. 13 are the same as the processes from Step S101 to Step S107 illustrated in FIG. 9, and therefore, explanation thereof will be omitted.

The ideal position calculation unit 218 calculates the straight line 181 that connects the target position 180 in the display screen 101S and the pupil center 112C defined in the global coordinate system (Step S308).

Subsequently, the ideal position calculation unit 218 obtains, as the ideal corneal curvature center 110F, a point which is located on the straight line 181 calculated at Step S308 and for which a distance from the pupil center 112C is equal to the distance 126 that is obtained in the first calibration process, and calculates a position of the ideal corneal curvature center 110F (Step S309).

Subsequently, the arithmetic unit 220 calculates, for each of the right and left eyeballs, the positional difference 127 that is a distance between the ideal corneal curvature center 110F and the corrected corneal curvature center 110H (Step S310). The arithmetic unit 220 stores the calculated positional difference 127 in the storage unit 224. The positional difference 127 is used as a calibration value for the corrected corneal curvature center 110H that is obtained in the gaze point detection process. For example, when the gaze point detection process is performed at a later time, the gaze point detection unit 216 detects a line-of-sight direction of each of the right and left eyeballs from the position of the pupil center 112C and a position that is obtained by adding the positional difference 127 to the position of the corrected corneal curvature center 110H. Specifically, the gaze point detection unit 216 detects, as a calibrated line-of-sight direction of the subject, a line-of-sight vector from a corneal curvature center, which is obtained by adding the positional difference 127 as the calibration value to the corrected corneal curvature center 110H, to the pupil center 112C.

Validity Determination Process

Next, the validity determination process (S400) will be described. The validity determination process (S400) includes calculation of the right-left difference that is a difference between the positional differences 127 of the right and left eyeballs and determination on whether the line-of-sight direction of each of the right and left eyeballs is valid based on a magnitude of the right-left difference, for each of the right and left eyeballs.

Figure 14:
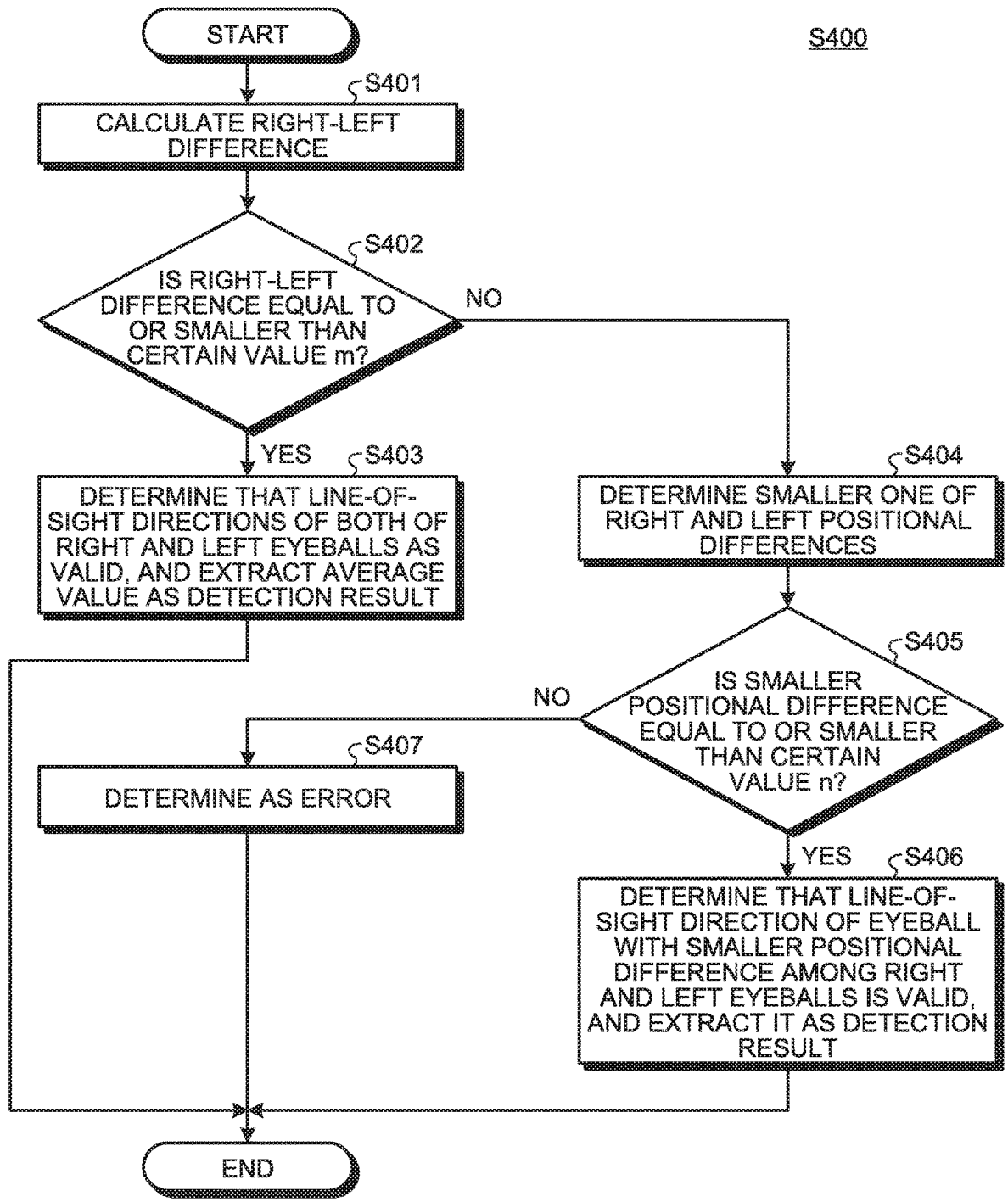
FIG. 14 is a flowchart illustrating an example of a validity determination process according to the present embodiment.

FIG. 14 is a flowchart illustrating an example of the validity determination process (S400) according to the present embodiment. As illustrated in FIG. 14, in the validity determination process S400, the arithmetic unit 220 calculates the right-left difference that is a difference between the positional differences 127 of the right and left eyeballs (Step S401).

After calculating the right-left difference, the determination unit 222 determines whether an absolute value of the right-left difference is equal to or smaller than a certain value m (a first threshold value or a predetermined threshold) (Step S402). The certain value m is set and stored in the storage unit 224 in advance. If the determination unit 222 determines that the absolute value of the right-left difference is equal to or smaller than the certain value m (Yes at Step S402), the gaze point detection unit 216 determines that the line-of-sight directions of both of the right and left eyeballs are valid, and extracts an average value of the right and left line-of-sight directions as a detection result (Step S403).

In contrast, at Step S402, if the determination unit 222 determines that the absolute value of the right-left difference is larger than the certain value m (No at Step S402), the determination unit 222 determines which of the right and left positional differences 127 is smaller (Step S404). At Step S404, the arithmetic unit 220 is able to easily determine which of the right and left positional differences is smaller by determining that the positional difference 127 of the right eyeball is smaller when a subtraction value obtained by subtracting the positional difference 127 of the right eyeball from the positional difference 127 of the left eyeball is a positive value, and by determining that the positional difference 127 of the left eyeball is smaller when the subtraction value is a negative value, for example. Meanwhile, the arithmetic unit 220 may perform the same determination on a subtraction value that is obtained by subtracting the positional difference 127 of the left eyeball from the positional difference 127 of the right eyeball.

Subsequently, the arithmetic unit 220 determines whether the smaller one of the right and left positional differences 127 is equal to or smaller than a certain value n (second threshold) (Step S405). The certain value n is set and stored in the storage unit 224 in advance. At Step S405, if the determination unit 222 determines that the smaller positional difference 127 is equal to or smaller than the certain value n (Yes at Step S405), the gaze point detection unit 216 determines that the line-of-sight direction of the eyeball with the smaller positional difference 127 among the right and left eyeballs is valid, and extracts the line-of-sight direction as a detection result (Step S406).

In contrast, at Step S405, if the determination unit 222 determines that the smaller positional difference 127 is larger than the certain value n (No at Step S405), the determination unit 222 determines that the line-of-sight directions of both of the right and left eyeballs are not valid and determines them as error (Step S407). The validity determination process is terminated if any of Step S403, Step S406, and Step S407 is performed.

As described above, the line-of-sight detection device 100 according to the present embodiment includes: the display control unit 202 that displays an image at a single point on the display screen 101S of the display device 101; the lighting device 103 that irradiates the right and left eyeballs of the subject with detection light; the image data acquisition unit 206 that acquires image data of the right and left eyeballs of the subject irradiated with the detection light; the position detection unit 210 that detects, from the acquired image data, the position of the pupil center 112C and the position of the corneal reflection center 113C of each of the right and left eyeballs; the curvature center calculation unit 212 that calculates the position of the corneal curvature center 110 of each of the right and left eyeballs on the basis of the straight line 131 connecting the light source 103 and the corneal reflection center 113C and the straight line 132 connecting the image and the pupil center 112C; the corrected position calculation unit 214 that corrects the position of the corneal curvature center 110 on the basis of the distance between the pupil center 112C and the corneal curvature center 110, and calculates the position of the corrected corneal curvature center 110H of each of the right and left eyeballs; the ideal position calculation unit 218 that calculates the position of the ideal corneal curvature center 110F of each of the right and left eyeballs from the position of the image displayed at the single point on the display screen 101S and the position of the pupil center 112C; the arithmetic unit 220 that calculates the positional difference 127 that is a difference between the position of the corrected corneal curvature center 110H and the position of the ideal corneal curvature center 110F for each of the right and left eyeballs; the gaze point detection unit 216 that detects the line-of-sight direction of each of the right and left eyeballs from the position of the pupil center 112C and the position that is obtained by adding the positional difference 127 to the corrected corneal curvature center 110H; and the determination unit 222 that determines whether the line-of-sight direction of each of the right and left eyeballs detected by the gaze point detection unit 216 is valid on the basis of the magnitude of the right-left difference that is a difference between the positional differences 127 of the right and left eyeballs.

With this configuration, the validity of the line-of-sight direction detected by the gaze point detection unit 216 is determined by using the positional difference 127 that is a calibration value used for detecting the position of the corneal curvature center, so that it is not necessary to additionally use a system or the like for detecting the validity of the line-of-sight direction, and it is possible to easily and effectively determine the validity of the line-of-sight direction. Consequently, it is possible to accurately detect line-of-sight directions of various subjects, such as a subject whose left and right eyeballs have different corneal curvature radii or a subject whose line-of-sight directions of left and right eyeballs are largely different due to the influence of strabismus or the like.

Furthermore, in the present embodiment, the arithmetic unit 222 calculates the right-left difference based on the calculated positional differences 127 of the right and left eyeballs, so that the arithmetic unit 222 is able to effectively calculate the positional differences 127 and the right-left difference.

Moreover, in the present embodiment, the gaze point detection unit 216 extracts, as a detection result, the line-of-sight direction that is determined as being valid by the determination unit 222 from the line-of-sight directions of the right and left eyeballs, so that it is possible to more reliably determine the validity of the line-of-sight direction.

Furthermore, in the present embodiment, if the absolute value of the right-left difference is equal to or smaller than the first threshold, the determination unit 222 determines that the line-of-sight directions of both of the right and left eyeballs are valid. Therefore, it is possible to improve determination accuracy in determining the validity of the line-of-sight direction.

Moreover, in the present embodiment, if the absolute value of the right-left difference is larger than the first threshold and the smaller positional difference 127 between the positional differences 127 of the right and left eyeballs is equal to or smaller than the second threshold, the determination unit 222 determines that the line-of-sight direction of the eyeball with the smaller positional difference 127 between the right and left eyeballs is valid. Therefore, it is possible to use only the valid line-of-sight direction between the right and left eyeballs. Consequently, it is possible to improve accuracy in determining the validity of the line-of-sight direction.

Furthermore, in the present embodiment, if the right-left difference is larger than the first threshold and the smaller positional difference 127 between the positional differences 127 of the right and left eyeballs is larger than the second threshold, the determination unit 222 determines that the line-of-sight directions of both of the right and left eyeballs are not valid, so that it is possible not to use invalid line-of-sight directions. Therefore, it is possible to improve accuracy in determining the validity of the line-of-sight direction.

The technical scope of the present disclosure is not limited to the embodiments as described above, but various modifications may be made appropriately within the scope not departing from the gist of the present disclosure.

For example, in the validity determination process (S400) of the above-described embodiment, after Step S401, the determination unit 222 may perform a process of determining whether the right-left difference that is a difference between the positional differences 127 of the right and left eyeballs is equal to or smaller than the certain value m (predetermined threshold) and outputting a determination result. Meanwhile, this process may be performed in parallel to the above-descried validity determination process, or this process may be performed as an independent validity determination process. Accordingly, it becomes possible to detect whether the line-of-sight directions of the right and left eyeballs of the subject are largely different based on an output result. With use of a detection result, it is possible to improve detection accuracy of the line-of-sight direction. According to the present disclosure, it is possible to accurately detect line-of-sight directions of various subjects.

What is claimed is:

1. A line-of-sight detection device comprising:
   a display control unit configured to display an image at a single point on a display screen of a display device;
   a light source configured to irradiate right and left eyeballs of a subject with detection light;
   an image data acquisition unit configured to acquire image data of the right and left eyeballs of the subject irradiated with the detection light;
   a position detection unit configured to detect, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs;
   a curvature center calculation unit configured to calculate a position of a corneal curvature center of each of the right and left eyeballs on the basis of a virtual line connecting the light source and the corneal reflection center and a virtual line connecting the image and the pupil center;
   a corrected position calculation unit configured to correct the position of the corneal curvature center on the basis of a distance between the pupil center and the corneal curvature center, and calculate a position of the corrected corneal curvature center of each of the right and left eyeballs;
   an ideal position calculation unit configured to calculate a position of an ideal corneal curvature center of each of the right and left eyeballs from a position of the image displayed at the single point on the display screen and the position of the pupil center;
   an arithmetic unit configured to calculate a positional difference that is a difference between the position of the corrected corneal curvature center and the position of the ideal corneal curvature center for each of the right and left eyeballs;
   a gaze point detection unit configured to detect a line-of-sight direction of each of the right and left eyeballs from the position of the pupil center and a position that is obtained by adding the positional difference to the position of the corrected corneal curvature center; and
   a determination unit configured to determine whether the line-of-sight direction of each of the right and left eyeballs detected by the gaze point detection unit is valid on the basis of a magnitude of a right-left difference that is a difference between the positional differences of the right and left eyeballs.

2. The line-of-sight detection device according to claim 1, wherein if an absolute value of the right-left difference is equal to or smaller than a first threshold, the determination unit determines that the line-of-sight directions of both of the right and left eyeballs are valid.

3. The line-of-sight detection device according to claim 1, wherein if the right-left difference is larger than the first threshold and a smaller positional difference between the positional differences of the right and left eyeballs is equal to or smaller than a second threshold, the determination unit determines that the line-of-sight direction of the eyeball with the smaller positional difference between the right and left eyeballs is valid.

4. A line-of-sight detection method comprising:
   a display control step of displaying an image at a single point on a display screen of a display device;
   an irradiation step of irradiating right and left eyeballs of a subject with detection light from a light source;
   an image data acquisition step of acquiring image data of the right and left eyeballs of the subject irradiated with the detection light;
   a position detection step of detecting, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs;
   a curvature center calculation step of calculating a position of a corneal curvature center of each of the right and left eyeballs on the basis of a virtual line connecting the light source and the corneal reflection center and a virtual line connecting the image and the pupil center;
   a corrected position calculation step of correcting the position of the corneal curvature center on the basis of a distance between the pupil center and the corneal curvature center, and calculating a position of the corrected corneal curvature center of each of the right and left eyeballs;
   an ideal position calculation step of calculating a position of an ideal corneal curvature center of each of the right and left eyeballs from a position of the image displayed at the single point on the display screen and the position of the pupil center;
   an arithmetic step of calculating a positional difference that is a difference between the position of the corrected corneal curvature center and the position of the ideal corneal curvature center for each of the right and left eyeballs;
   a gaze point detection step of detecting a line-of-sight direction of each of the right and left eyeballs from the position of the pupil center and a position that is obtained by adding the positional difference to the position of the corrected corneal curvature center; and
   a determination step of determining whether the line-of-sight direction of each of the right and left eyeballs is valid on the basis of a magnitude of a right-left difference that is a difference between the positional differences of the right and left eyeballs.

5. A non-transitory storage medium storing a line-of-sight detection program therein that causes a computer to execute:
a display control step of displaying an image at a single point on a display screen of a display device;
an irradiation step of irradiating right and left eyeballs of a subject with detection light from a light source;
an image data acquisition step of acquiring image data of the right and left eyeballs of the subject irradiated with the detection light;
a position detection step of detecting, from the acquired image data, a position of a pupil center and a position of a corneal reflection center of each of the right and left eyeballs, the pupil center indicating a center of a pupil of each of the right and left eyeballs, the corneal reflection center indicating a center of corneal reflection of each of the right and left eyeballs;
a curvature center calculation step of calculating a position of a corneal curvature center of each of the right and left eyeballs on the basis of a virtual line connecting the light source and the corneal reflection center and a virtual line connecting the image and the pupil center;
a corrected position calculation step of correcting the position of the corneal curvature center on the basis of a distance between the pupil center and the corneal curvature center, and calculating a position of the corrected corneal curvature center of each of the right and left eyeballs;
an ideal position calculation step of calculating a position of an ideal corneal curvature center of each of the right and left eyeballs from a position of the image displayed at the single point on the display screen and the position of the pupil center;
an arithmetic step of calculating a positional difference that is a difference between the position of the corrected corneal curvature center and the position of the ideal corneal curvature center for each of the right and left eyeballs;
a gaze point detection step of detecting a line-of-sight direction of each of the right and left eyeballs from the position of the pupil center and a position that is obtained by adding the positional difference to the position of the corrected corneal curvature center; and
a determination step of determining whether the line-of-sight direction of each of the right and left eyeballs is valid on the basis of a magnitude of a right-left difference that is a difference between the positional differences of the right and left eyeballs.

* * * * *